US 9,757,073 B2

(12) United States Patent
Goshen et al.

(10) Patent No.: US 9,757,073 B2
(45) Date of Patent: Sep. 12, 2017

(54) FRACTIONAL FLOW RESERVE (FFR) INDEX

(71) Applicant: KONINKLIJKE PHILIPS N.V., Eindhoven (NL)

(72) Inventors: Liran Goshen, Pardes-Hanna (IL); Yechiel Lamash, Haifa (IL); Guy Gilboa, Kiryat Tivon (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 191 days.

(21) Appl. No.: 14/437,990

(22) PCT Filed: Oct. 24, 2013

(86) PCT No.: PCT/IB2013/059616
§ 371 (c)(1),
(2) Date: Apr. 23, 2015

(87) PCT Pub. No.: WO2014/072861
PCT Pub. Date: May 15, 2014

(65) Prior Publication Data
US 2015/0282765 A1    Oct. 8, 2015

Related U.S. Application Data

(60) Provisional application No. 61/722,814, filed on Nov. 6, 2012.

(51) Int. Cl.
*G06K 9/00* (2006.01)
*A61B 5/00* (2006.01)
(Continued)

(52) U.S. Cl.
CPC ............ *A61B 5/7267* (2013.01); *A61B 5/021* (2013.01); *A61B 5/02007* (2013.01);
(Continued)

(58) Field of Classification Search
None
See application file for complete search history.

(56) References Cited

U.S. PATENT DOCUMENTS

| 8,157,742 B2 | 4/2012 | Taylor |
| 8,200,466 B2 | 6/2012 | Spilker |

(Continued)

FOREIGN PATENT DOCUMENTS

| DE | 102008014792 | 6/2009 |
| WO | 2004025572 | 3/2004 |

(Continued)

OTHER PUBLICATIONS

Barnes, E.; CTA becomes a one-stop shop with FFR measurement; Aug. 15, 2011; http://www.auntminnie.com accessed Aug. 23, 2012.

(Continued)

*Primary Examiner* — Manuchehr Rahmjoo

(57) ABSTRACT

As described herein, an unknown FFR is classified based on certain extracted features. In addition, an estimation of the unknown FFR can be determined based on certain extracted features. Furthermore, a confidence interval can be determined for the estimated FFR. In another instance, boundary conditions for determining an FFR via simulation are determined. The boundary conditions can be used to classify the unknown FFR.

19 Claims, 5 Drawing Sheets

(51) Int. Cl.

| | |
|---|---|
| A61B 6/03 | (2006.01) |
| A61B 6/00 | (2006.01) |
| A61B 5/02 | (2006.01) |
| A61B 5/021 | (2006.01) |
| A61B 5/026 | (2006.01) |
| A61B 5/107 | (2006.01) |

(52) U.S. Cl.
CPC .......... *A61B 5/0263* (2013.01); *A61B 5/1075* (2013.01); *A61B 6/032* (2013.01); *A61B 6/504* (2013.01); *A61B 6/507* (2013.01); *A61B 6/5217* (2013.01)

(56) References Cited

U.S. PATENT DOCUMENTS

| | | |
|---|---|---|
| 8,249,815 B2 | 8/2012 | Taylor |
| 2010/0130878 A1 | 5/2010 | Lasso |
| 2010/0241404 A1 | 9/2010 | Taylor et al. |
| 2011/0307231 A1 | 12/2011 | Kirchner |
| 2012/0022843 A1 | 1/2012 | Ionasec |
| 2012/0041318 A1 | 2/2012 | Taylor |
| 2012/0041319 A1 | 2/2012 | Taylor |
| 2012/0041320 A1 | 2/2012 | Taylor |
| 2012/0041321 A1 | 2/2012 | Taylor |
| 2012/0041322 A1 | 2/2012 | Taylor |
| 2012/0041323 A1 | 2/2012 | Taylor |
| 2012/0041324 A1 | 2/2012 | Taylor |
| 2012/0041735 A1 | 2/2012 | Taylor |
| 2012/0041739 A1 | 2/2012 | Taylor |
| 2012/0053919 A1 | 3/2012 | Taylor |
| 2012/0059246 A1 | 3/2012 | Taylor |
| 2012/0072190 A1 | 3/2012 | Sharma et al. |
| 2012/0121151 A1 | 5/2012 | Bernhardt |
| 2012/0243761 A1 | 9/2012 | Senzig |
| 2016/0133015 A1 | 5/2016 | Taylor |

FOREIGN PATENT DOCUMENTS

| | | |
|---|---|---|
| WO | 2006061814 | 6/2006 |
| WO | 2006061815 | 6/2006 |
| WO | 2010022762 | 3/2010 |
| WO | 2012021307 A2 | 2/2012 |

OTHER PUBLICATIONS

De Caterina, A.R., et al.; Limitations of Noninvasive Measurement of Fractional Flow Reserve From Coronary Computed Tomography Angiography; 2012; J. Am. Coll. Cardiol.; 59:1408-1409.

Erglis, A., et al.; Non-invasive FFR Using Coronary CT Angiography and Computational Fluid Dynamics Predicts the Hemodynamic Significance of Coronary Lesions; Aug. 29, 2010; Pauls Stradins Clinical University Hospital, Riga, Latvia.

Huo, Y., et al.; Intraspecific scaling laws of vascular trees; 2011; J. R. Soc. Interface; http://rsif.royalsocietypublishing.org downloaded Jun. 17, 2011.

Huo, Y., et al.; A Scaling Law of Vascular Volume; 2009; Biophysical Journal; vol. 96:347-353.

Kern, M. J., et al.; Current Concepts of Integrated Coronary Physiology in the Catheterization Laboratory; 2010; Journal of the American College of Cardiology; 55:173-185.

Kim, H. J., et al.; Patient-Specific Modeling of Blood Flow and Pressure in Human Coronary Arteries; 2010; Annals of Biomedical Engineering; 38(10)3195-3209.

Kim, H. J., et al.; Incorporating Autoregulatory Mechanisms of the Cardiovascular System in Three-Dimensional Finite Element Models of Arterial Blood Flow; 2010; Annals of Biomedical Engineering; 38(7)2314-2330.

Koo, B-K., et al.; Diagnosis of Ischemia-Causing Coronary Stenoses by Noninvasive Fractional Flow Reserve computed from Coronary Computed Tomographic Angiograms; 2011; J. Am. Coll. Cardiol.; 58(19)1989-1997.

Pijls, N. H. J., et al.; Measurement of Fractional Flow Reserve to Assess the Functional Severity of Coronary-Artery Stenoses; 1996; The New England Journal of Medicine; 334(26)1703-1708.

Pijls, N. H. J., et al.; Fractional Flow Reserve: A Useful Index to Evaluate the Influence of an Epicardial Coronary Stenosis on Myocardial Blood Flow; 1995; Circulation; 92:3183-3193.

Smitha, P., et al.; A Review of Medical Image Classification Techniques; 2011; International Journal of Computer Applications; http://www.ijcaonline.org/icvci/number11/icvci1458.pdf.

Taylor, C. A., et al.; Patient-Specific Modeling of Cardiovascular Mechanics; 2009; Annu. Rev. Biomed. Eng.; 11:109-134.

Vignon-Clementel, I. E., et al.; Outflow boundary conditions for three-dimensional simulations of non-periodic blood flow and pressure fields in deformable arteries; 2006; J. of Biomechanis; vol. 39:S431.

FRACTIONAL FLOW RESERVE (FFR) INDEX

CROSS REFERENCE TO RELATED APPLICATIONS

This application is a national fling of PCT application Serial No. PCT/IB2013/059616, filed Oct. 24, 2013, published as WO 2014/072861 A2 on May 15, 2014, which claims the benefit of U.S. provisional application Ser. No. 61/722,814 filed Nov. 6, 2012, which is incorporated herein by reference.

The following generally relates to the fractional flow reserve index and is described with particular application to computed tomography (CT). However, the following is also amenable to other imaging modalities including X-ray, magnetic resonance imaging (MRI), and/or other imaging modalities.

FFR is an index of the functional severity of a coronary stenosis that is calculated from pressure measurements made during coronary arteriography and is defined as the distal blood pressure (behind a stenosis) relative to the proximal pressure (close to the Ostium) under hyperemic conditions. In other words, the FFR index expresses the maximal flow down a vessel in the presence of a stenosis compared to the maximal flow in the hypothetical absence of the stenosis. The FFR value is an absolute number between 0 and 1, where a value 0.50 indicates that a given stenosis causes a 50% drop in blood pressure, and facilitates diagnosis of the extent of a stenosis.

The FFR index has been measured using a pressure wire to obtain the blood pressure before and after the stenosis. For example, during coronary catheterization, a catheter is inserted into the femoral or radial arteries using a sheath and guide wire. A sensor, affixed to the tip of the catheter, is positioned at the stenosis. The catheter and hence the sensor is pulled back and the sensor senses pressure, temperature and flow, which are recorded, across the stenosis, during conditions promoted by various agents that effect vessel geometry, compliance and resistance, and/or other characteristics. Unfortunately, this approach is costly and minimally invasive, exposing the patient to health risk.

A non-invasive approach to estimating the FFR index is through computational fluid dynamic (CFD) simulations in which blood flow and pressure through the coronaries is simulated. For this approach, the 3D coronary geometry is based on a cardiac CT scan of the patient. Unfortunately, with this approach, the boundary conditions (i.e., flow, pressure and/or resistance) outside the extracted geometry are not well-defined, and the values of flow and pressure at the inlet (ostium) and vessel-outlets greatly affect the FFR estimation accuracy. This approach is also time costly, requiring intensive computations (e.g., up to hours) and assumes very high quality geometrical data (e.g., coronary segmentation), which often implies significant manual editing.

Aspects described herein address the above-referenced problems and others.

As described below, an unknown FFR is classified based on certain extracted features. In addition, an estimation of the unknown FFR can be determined based on certain extracted features. Furthermore, a confidence interval can be determined for the estimated FFR. In another instance, boundary conditions for determining an FFR via simulation are determined. The boundary conditions can be used to classify the unknown FFR.

In one aspect, a method includes classifying an unknown fractional flow reserve metric for a cardiac vessel with a stenosis as one of a plurality of different pre-defined classes based on extracted features and a learning model, and generating a signal indicative of the classification, wherein the extracted features are extracted from segmented image data segmented from image data in that includes a representation of the cardiac vessel and the stenosis.

In another aspect, a method includes estimating an unknown fractional flow reserve metric for a stenosis of a cardiac vessel into one of a plurality of different pre-defined classes based on extracted features and a learning model, and generating a signal indicative of the estimation, wherein the extracted features are extracted from segmented image data segmented from image data in that includes a representation of the cardiac vessel and the stenosis.

In another aspect, a method includes estimating a boundary condition of a stenosis of a vessel, including at least one of an estimated outlet flow rate of the stenosis or an estimated outlet resistance of the stenosis, based on image data that includes a representation of the vessel and the stenosis.

In another aspect, a system includes a data analyzer that determines at least one of a fractional flow reserve classification of an unknown fractional flow reserve for a stenosis, an estimated fractional flow reserve of the stenosis based on the classification or a confidence interval for the estimated fractional flow reserve, or at least one boundary condition of the stenosis for a computational fluid dynamics simulation to determine a fractional flow reserve for the stenosis.

The invention may take form in various components and arrangements of components, and in various steps and arrangements of steps. The drawings are only for purposes of illustrating the preferred embodiments and are not to be construed as limiting the invention.

FIG. 1 schematically illustrates an imaging system in connection with a data analyzer.

The following describes non-limiting approaches for classifying an unknown FFR based on certain extracted features, estimating the FFR based on certain extracted features, determining a confidence interval for the estimated FFR and/or determining boundary conditions for determining an FFR via simulation.

Figure 1:
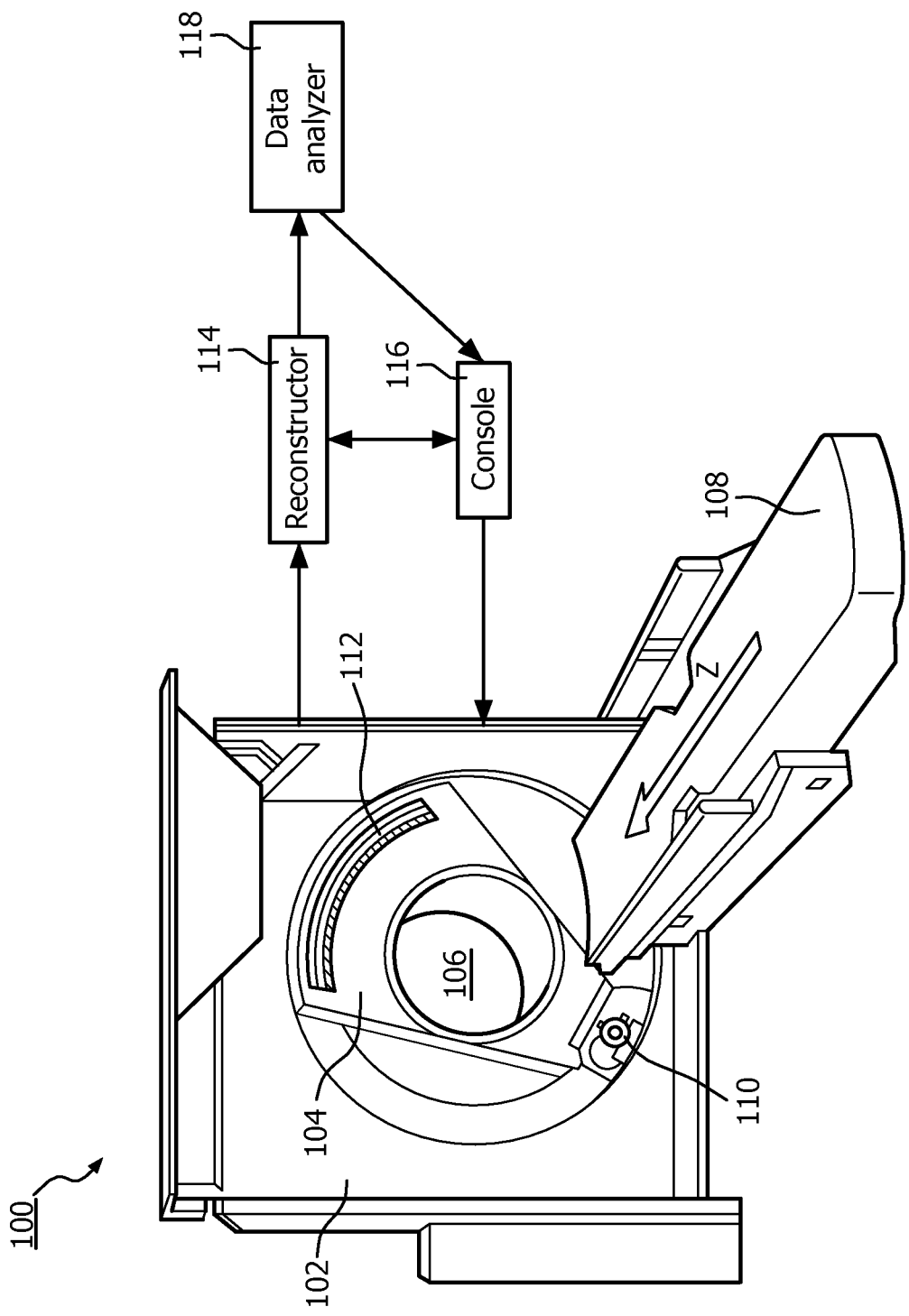

FIG. 1 schematically illustrates an imaging system 100 such as a CT scanner. The imaging system 100 includes a generally stationary gantry 102 and a rotating gantry 104, which is rotatably supported by the stationary gantry 102 and rotates around an examination region 106 about a z-axis. A subject support 108, such as a couch, supports an object or subject in the examination region 106.

A radiation source 110, such as an x-ray tube, is rotatably supported by the rotating gantry 104, rotates with the rotating gantry 104, and emits radiation that traverses the examination region 106. A radiation sensitive detector array 112 subtends an angular arc opposite the radiation source 110 across the examination region 106. The radiation sensitive detector array 112 detects radiation traversing the examination region 106 and generates a signal indicative thereof for each detected photon.

A reconstructor 114 reconstructs the projection, generating volumetric image data indicative of a scanned portion of a subject or object located in the examination region 106. A general-purpose computing system or computer serves as an operator console 116. The console 116 includes a human readable output device such as a monitor and an input device such as a keyboard, mouse, etc. Software resident on the console 116 allows the operator to interact with and/or operate the scanner 100 via a graphical user interface (GUI) or otherwise.

A data analyzer 118 is configured to at least process image data representing a vessel(s) (e.g., coronary arteries, cerebral artery, etc.) of interest, including a stenosis thereof. The image data can be generated by the imaging system 100 and/or other imaging system. As described in greater detail below, in one non-limiting instance, the data analyzer 118 determines features such as boundary conditions (e.g., flow, pressure, and/or resistance) outside the stenosis and employs these features using a computational fluid dynamics approach to determine an FFR value for the stenosis.

Also described in greater detail below, the data analyzer 118 can also at least one of: classifies an unknown FFR into one of a set of predetermined classifications based on certain features, estimates an FFR based on certain features, or determines a confidence interval for an estimated FFR. The foregoing allows non-invasive, robust, accurate and fast simulation boundary condition determination, FFR classification and/or estimation (with or without the a confidence interval) with simplified workflow, shorter estimation time, and less burden on the user.

The data analyzer 118 can be implemented with one or more processors of one or more computing systems that execute one or more computer readable instructions stored in one or more computer readable storage mediums, such as physical memory and/or other non-transitory storage medium. The processor(s) may additionally or alternatively execute one or more computer readable instructions carried by a carrier wave, a signal and/or other transitory medium.

Figure 2:
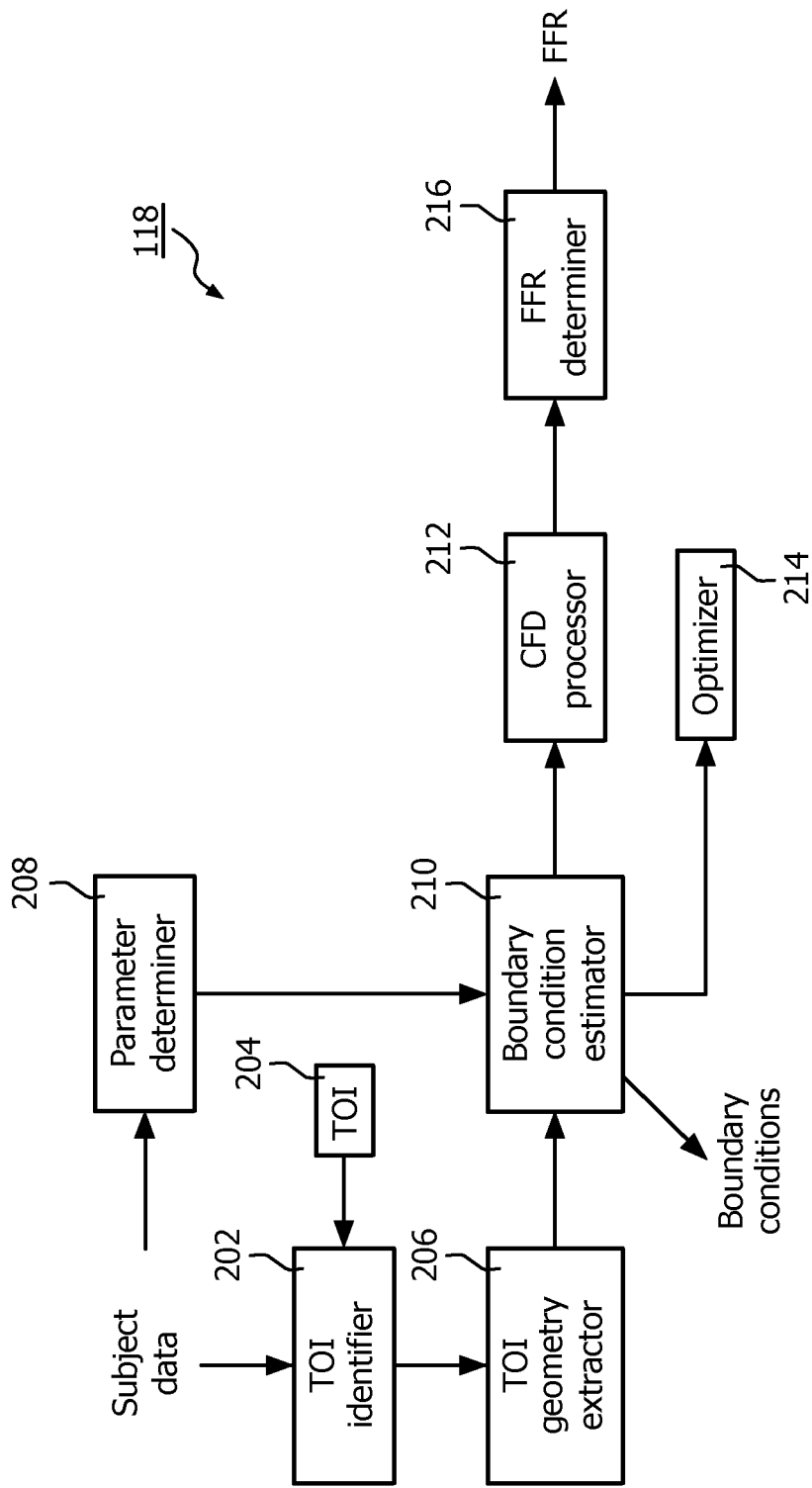
FIG. 2 illustrates an example of the data analyzer of FIG. 1.

FIG. 2 illustrates an example of the data analyzer 118.

A tissue of interest (TOI) identifier 202 obtains, as input, subject data, including image data representative of tissue of interest (TOI) 204 and identifies the tissue of interest 204 in the image data. The tissue of interest 204 can be predetermined or identified by a signal indicative of a user selected tissue of interest, a default tissue of interest, etc. The TOI identifier 202 can employ automatic and/or manual approaches to identify the tissue of interest. An example of tissue of interest is tubular tissue such as a vessel with a stenosis. However, the tissue of interest can be other tissue.

A TOI geometry extractor 206 extracts geometrical information from the identified tissue of interest. The TOI identifier 202 can employ automatic and/or manual approaches to extract the geometrical information. By way of example, the extraction may include employing segmentation with active-contours and level-sets tuned for coronary vessels where the tissue of interest is the coronary vessels, followed by optional additional manual editing to produce high quality segmentation. From this and/or other extraction, an effective diameter at the ostium $D_o$ and/or other tissue of interest geometry can be determined.

A parameter determiner 208 determines at least one parameter based on the subject data. For example, in the context of vessel stenosis, the parameter determiner 208 can determine an inlet flow-rate $Q_o$ (i.e., flow rate at the ostium). This can be achieved based on subject data such as weight, body mass index (BMI), gender, age, blood test results, anatomical imaging data (e.g., myocardium mass and estimated stroke-volume), and/or subject data. Generally, this data is treated as features for a training set using of a classifier such as a support vector machine (SVM), random forests and/or other classifier. In this instance, "ground truth" data to train the model can include information from cardiac catheterization procedures, for example, data from a flow-rate meter such as a Doppler-tipped guide wire and/or other apparatus.

A boundary condition estimator 210 estimates at least one boundary condition (e.g., flow rate Q, average velocity, resistance, etc. of vessel outlets) based on the geometry extracted (e.g., diameter at the ostium $D_o$) by the TOI geometry extractor 206 and the parameter determined (e.g., the inlet flow-rate $Q_o$) by the parameter determiner 208. By way of example, the boundary condition estimator 210 can estimate a flow rate boundary condition Q at the outlet as a function of $Q_o$ and $D_o$ as shown in EQUATION 1:

$$Q = Q_o \left(\frac{D}{D_o}\right)^{\frac{7}{3}}, \qquad \text{EQUATION 1}$$

where D is the effective diameter at each outlet. An average velocity can be determined as shown in EQUATION 2:

$$v = \frac{\pi}{4} K D^{\frac{1}{3}}. \qquad \text{EQUATION 2}$$

The boundary condition estimator 210 can estimate a resistance boundary condition as shown in EQUATION 3:

$$R \stackrel{\text{def}}{=} \frac{P}{Q}. \qquad \text{EQUATION 3}$$

For healthy vessels, $P_o \cong P$, where $P_o$ is the aortic pressure at the ostium, which can be determined by measuring the brachial blood pressure, and the resistance of healthy tissue $R_h$ can be determined based on EQUATION 4:

$$R_h \cong \frac{P_o}{Q_o \left(\frac{D}{D_o}\right)^{\frac{7}{3}}}. \qquad \text{EQUATION 4}$$

For stenotic vessels, the pressure can drop considerably. As such, the ostium pressure may not be a reliable estimate, and the resistance of stenotic tissue $R_s$ can be estimated based on the following iterative approach:

1. Initialize by $$R_s^o = \frac{P_o}{Q_o \left(\frac{D}{D_o}\right)^{\frac{7}{3}}},$$

2. Run a fast coarse CFD simulation, and use the derived outlet pressure to update the resistance by:

$$R_s^{i+1} = \frac{P_i}{Q_o \left(\frac{D}{D_o}\right)^{\frac{7}{3}}},$$

and

3. Repeat until $R_s^{i+1} - R_s^i < \epsilon$.

A CFD processor 212 performs a computational fluid dynamic (CFD) simulation, for example, using partial-differential-equations. Generally, CFD is a fluid mechanics approach that uses numerical methods and/or algorithms to solve and analyze problems that involve fluid flows. The CFD processor 212 performs the calculations with surfaces defined by boundary conditions determined by the boundary condition estimator 210. However, other boundary conditions can also be employed. The output, in one instance, includes full volumetric information of pressure and velocity at all points.

An optional optimizer 214 can be used to optimize the boundary conditions. The CFD simulation yields both outlet velocity and pressure, by which outlet resistance can be calculated; outlet velocities are determined based on resistance boundary conditions and outlet resistance is determined based on velocity boundary conditions. As such, the boundary conditions can be optimized by minimizing energy, as shown in EQUATION 5:

$$E = \sum_{vessel\ i=1}^{n} (\hat{R}_i - R_i)^2 + \alpha(\hat{v}_i - v_i)^2 \qquad \text{EQUATION 5}$$

where $\hat{R}_t$ and $\hat{v}_t$ are determined based on a coarse CFD simulation.

An FFR determiner 216 determines an FFR based on the CFD results. This includes determining the FFR based on the estimated and/or optimized estimated boundary conditions. This approach provides a more accurate FFR determination relative to determining the FFR without the boundary conditions estimated by the boundary condition estimator 210 such as in approaches in which the boundary conditions outside the extracted geometry are not well-defined.

The boundary conditions estimated by the boundary conditions estimator 210 can optionally be used in connection with the data analyzer 118 of FIG. 3, as described in greater detail below.

Figure 3:
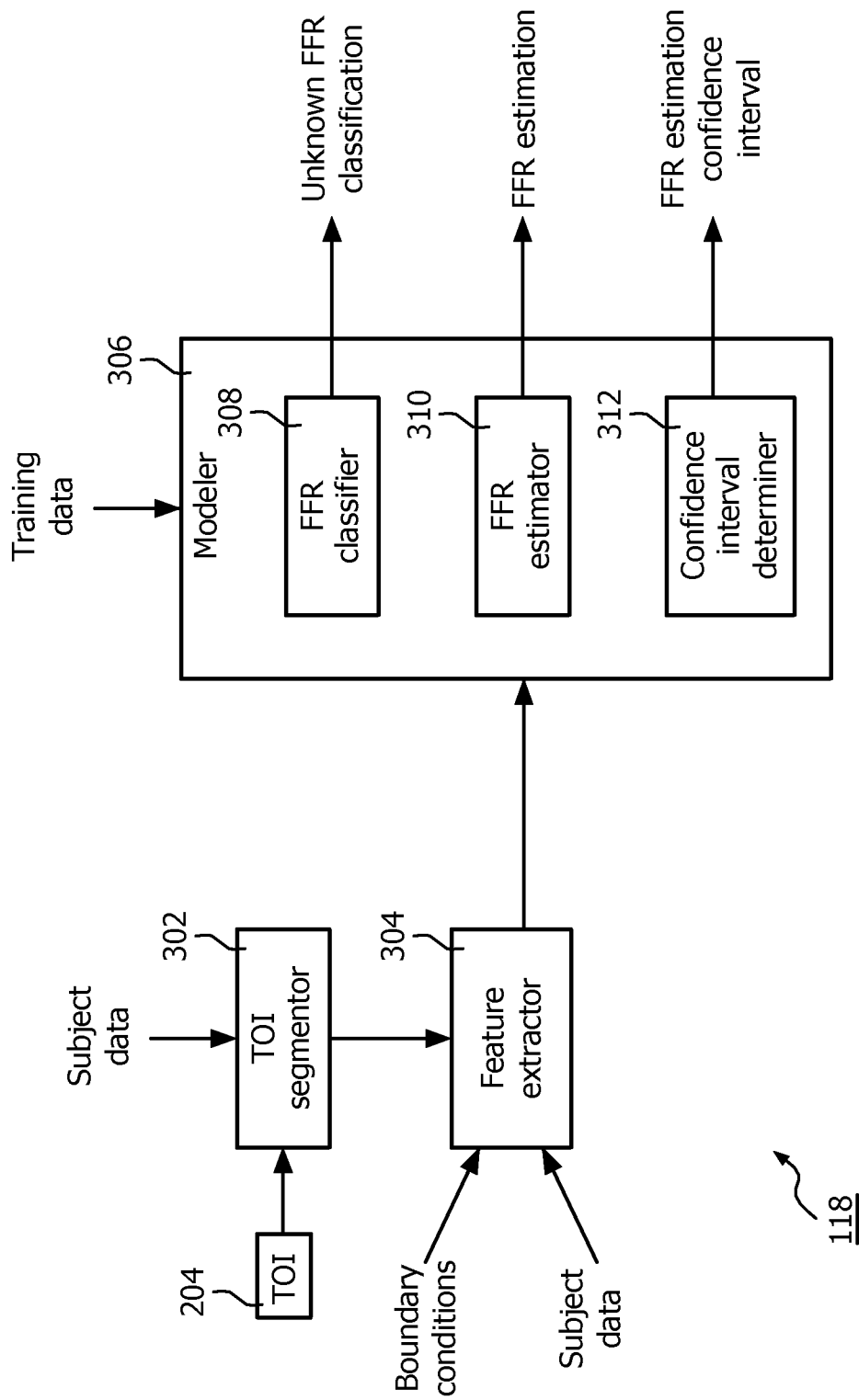
FIG. 3 illustrates another example of the data analyzer of FIG. 1.

FIG. 3 illustrates another example of the data analyzer 118.

A tissue of interest (TOI) segmentor 302 obtains, as input, subject data and segments the tissue of interest (TOI) 204 from image data therein. As discussed above, the tissue of interest 204 can be predetermined or identified by a signal indicative of a user selected tissue of interest, a default tissue of interest, etc. The TOI segmentor 302 can employ automatic and/or manual approaches to segment the tissue of interest. For cardiac applications, this includes segmenting at least a portion of the heart, for example, including coronaries segmentation and labeling, coronaries center line extraction, heart chambers segmentation and labeling, etc.

A feature extractor 304 extracts features. This includes extracting features from the subject data, the segmented data, boundary conditions and/or other information. Examples of boundary conditions include, but are not limited to, those estimated by the boundary conditions estimator 210 of FIG. 2 and/or other boundary conditions. Examples of features from the segmented data include, but are not limited to: stenosis percentage, stenosis length, distance between the aorta and the stenosis, stenosis position (artery label), heart geometry details, e.g., chamber sizes, myocardium mass, coronaries geometry details, coronaries center line details, and/or other information.

Examples of features from the image data include, but are not limited to: an $i^{th}$ percentile of HU (or sub-set of intensities) around the inlet of the stenosis region, an $i^{th}$ percentile of HU around the middle to the stenosis region, an $i^{th}$ percentile of HU around the outlet to the stenosis region, median HU after stenosis/median HU before stenosis, HU profile in around the inlet, outlet and center of the stenosis region, an HU profile along the whole vessel, and/or other information. Examples of features from the subject data include, but are not limited to: test results (e.g., Hemoglobin), vital signs (e.g., blood pressure, etc.), patient clinical history, patient family clinical history, and/or other information.

A modeler 306 includes one or more of an FFR classifier 308, an FFR estimator 310, and/or a confidence level determiner 312. The modeler 306 is pre-trained, for example, with a training set with "ground truth" results, for example, from prior cath-lab procedures of patients. The modeler 306 can be statistical or machine learning based, e.g., linear discriminant analysis (LDA), optimal discriminant analysis (QDA), naive Bayes, support vector machine (SVM), randomized trees, polynomial functions, mixture of Gaussians, decision trees, neural networks, etc.

Generally, a machine learning model is a function that obtains a vector of numbers (or pattern) as input and outputs a single value. The vector of numbers has a specific order of measurements, for example: blood pressure, age, gender, etc. Each element in the vector is called feature. In the illustrated example, the vector includes the above discussed features. The model contains parameters that can be adjusted given a new pattern. The training of model can be done using supervised learning or semi-supervised learning approaches.

The FFR classifier 308 classifies the unknown FFR as one of a predefined set of classes based on the extracted features. In this case, the output values are numbers that represent classes, for example class of "high risk", class of "med risk" and class of "low risk." An example of such a classification includes: non-significant (FFR>0.9); mild (0.8<FFR<0.9); severe (0.7<FFR<0.8), and very severe (FFR<0.7).

The FFR estimator 310 is configured to estimate a FFR, such as a point estimation. In one instance, the FFR estimator 310 performs the estimation using weighted interpolation based on k nearest neighbor samples from the whole training set or only from the related class set from the training set, where the related class is the class that was selected in the above FFR classification component and the training set is the set that was used to train the model.

The confidence interval determiner 312 is configured to estimate a confidence interval for the estimated FFR. The confidence interval is derived using the analyzed sample as the whole training set or only the related class set from the training set. The purpose of confidence interval is to give the estimated FFR a boundary of certainty. For example, an estimated FFR in 95% is in the interval [0.86, 0.95]. The narrower the interval is, the better the certainty.

Figure 4:
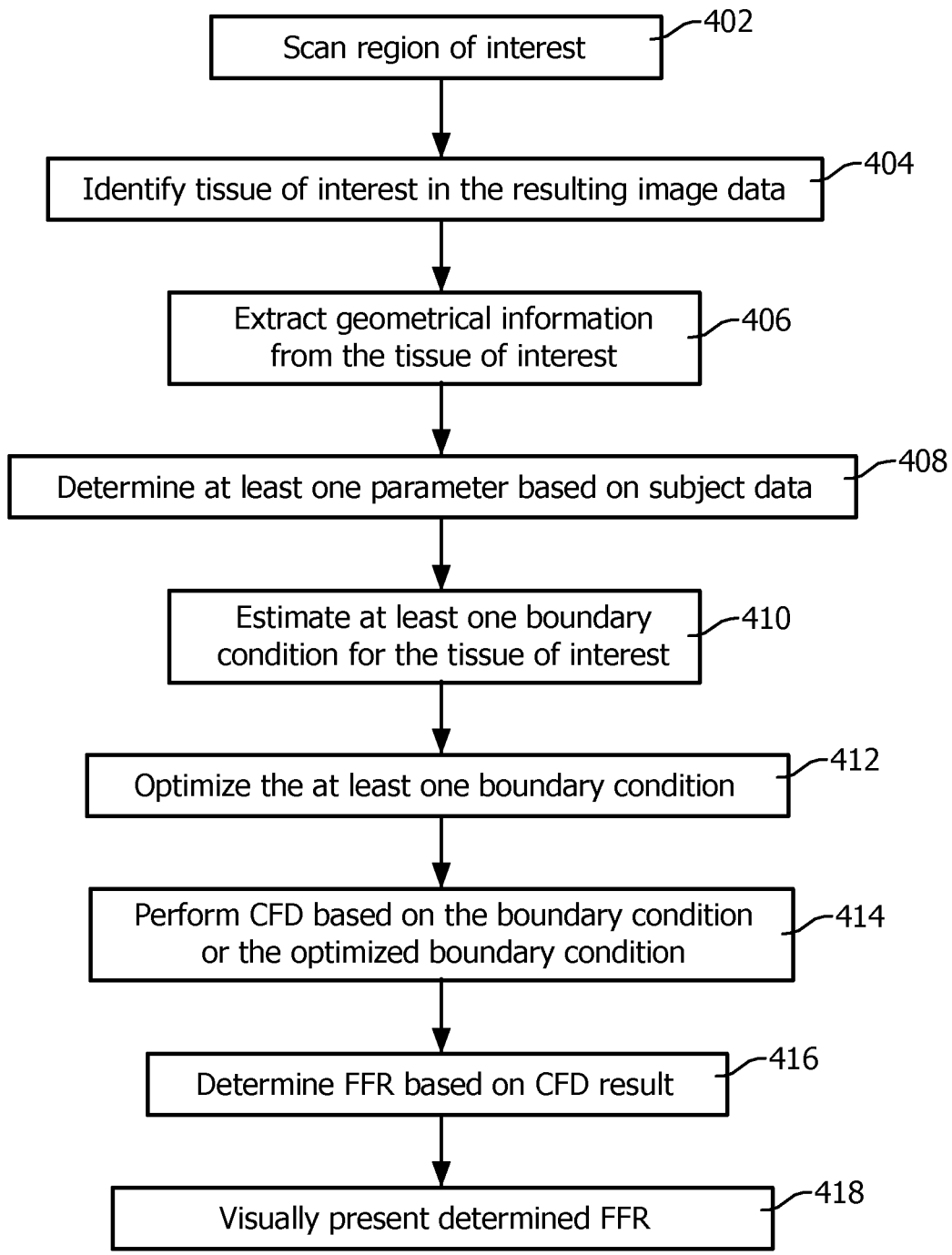
FIG. 4 illustrates an example method in accordance with the data analyzer of FIG. 2.

FIG. 4 illustrates an example method for determining an FFR.

At 402, a region of interest of a subject is scanned.

At 404, tissue of interest (e.g., a vessel with a stenosis) is identified in the image data from the scan corresponding to the region of interest.

At 406, geometrical information (e.g., diameter, radius, etc.) is extracted from the identified tissue of interest.

At 408, at least one parameter is determined based on subject data of the subject.

At 410, at least one boundary condition (e.g., flow rate Q, average velocity, resistance, etc. of vessel outlets) for the tissue of interest is estimated, e.g., based on the extracted geometrical information and the at least one parameter.

At 412, optionally, the at least one boundary condition is optimized.

At 414, a computational fluid dynamic (CFD) simulation is performed based on the at least one boundary condition or the optimized at least one boundary condition.

At 416, an FFR is determined for the tissue of interest based on the CFD results.

At 418, the FFR is visually presented.

Figure 5:
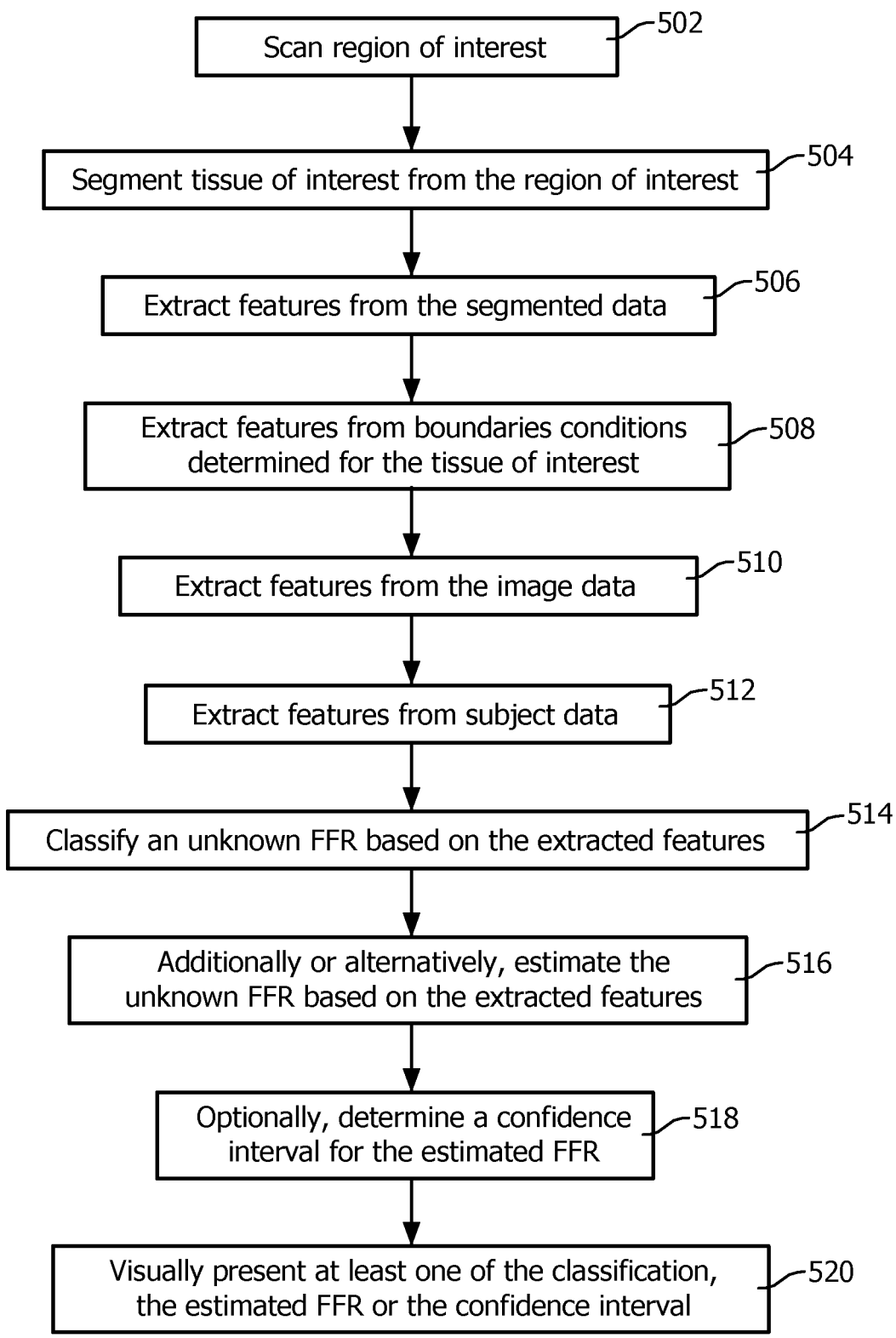
FIG. 5 illustrates an example method in accordance with the data analyzer of FIG. 3.

FIG. 5 illustrates an example method for at least classifying an unknown FFR.

At 502, a region of interest of a subject is scanned.

At 504, tissue of interest is segmented from the image data of the scan.

At 506, features are extracted from at least the segmented data.

At 508, features are extracted from the boundary conditions determined in FIG. 4.

At 510, features are extracted from the image data.

At 512, features are extracted from subject data such as test results, subject history, subject family history, etc.

Alternative and/or additional features are extracted in other examples.

At 514, an unknown FFR of the tissue of interest is classified as one of a predefined set of classes based on the extracted features.

At 516, additionally or alternatively, an FFR is estimated for the unknown FFR based on the extracted features.

At 518, optionally, a confidence interval for the estimated FFR is determined.

At 520, at least one of the classification, the estimated FFR or the confidence interval is visually presented.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium. It is to be appreciated that the ordering of the above acts is not limiting. As such, other orderings are contemplated herein. In addition, one or more acts may be omitted and/or one or more additional acts may be included.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
   estimating an outlet flow rate of a stenosis based on an effective diameter or radius at an outlet of the stenosis, a diameter or radius at an inlet of the stenosis, and a flow rate at the inlet of the stenosis, where at least one of the effective diameter or radius, the diameter or radius or the flow rate is determined based on image data produced by one of a computed tomography, an X-ray, or a magnetic resonance imaging system;
   iteratively estimating a resistance of the by:
      calculating an initial resistance as a function of aortic blood pressure at the inlet of the stenosis and the outlet flow rate;
      performing a coarse computational fluid dynamic simulation;
      generating a subsequent resistance based on the initial resistance and a result of the coarse computational fluid dynamic simulation, wherein the subsequent resistance is the estimated resistance; and
      repeating the acts of performing and generating using a current resistance until stopping iteration stopping criteria is satisfied;
   classifying an unknown fractional flow reserve metric for a cardiac vessel with the stenosis as one of a plurality of different pre-defined classes based on extracted features and a learning model, wherein the extracted features include one or more estimated boundary conditions of the stenosis, including at least one of the estimated outlet flow rate or the estimated outlet resistance of the stenosis; and
   generating a signal indicative of the classification.

2. The method of claim 1, wherein the classification includes generating a numerical value for the unknown FFR and, further comprising:
   classifying the unknown fractional flow reserve metric based on the numerical value.

3. The method of claim 1, wherein features include one or more of a stenosis percentage, a stenosis length, a distance between the aorta and the stenosis, a stenosis position, a heart chamber size, a myocardium mass, a geometry of a coronary artery, a center line of a coronary artery.

4. The method of claim 3, wherein the features include one or more of a subset of voxels corresponding to a set of intensities of interest around at least one of the inlet of the stenosis, a middle region of the stenosis or the outlet to the stenosis, a median intensity value of at least one of after the stenosis or before the stenosis, an intensity profile in around at least one of the inlet, the outlet or a center region of the stenosis, or an intensity profile along the vessel, one or more of test results, vital signs, subject history, or subject family history, or a result of a computational fluid dynamic simulation.

5. The method of claim 1, further comprising:
   optimizing the estimated resistance by minimizing an energy function including a resistance term and a flow velocity term.

6. The method of claim 5, further comprising:
   performing a subsequent computational fluid dynamics simulation based on the estimated outlet flow rate of the stenosis and the estimated resistance of the stenosis.

7. The method of claim 1, further comprising:
   estimating a point estimation of a fractional flow reserve for the stenosis and generating a second signal indicative thereof.

8. The method of claim 7, the estimating, comprising:
   using a weighted interpolation based on at least one of a predetermined number of nearest neighbor samples of a training set or only from a related class set from the training set, where the related class set is a class corresponding to the classification class.

9. The method of claim 7, further comprising:
   determining a confidence interval of the estimated fractional flow reserve and generating a third signal indicative thereof.

10. The method of claim 1, further comprising:
    determining the flow rate at the inlet of the stenosis using a machine learning algorithm trained with patient data, including at least one of image or non-image data, and flow rates measurements of other patients determined via cardiac catheterization.

11. The method claim 10, further comprising:
    determining a velocity based on the outlet flow rate.

12. The method of claim 1, further comprising:
    performing a subsequent computational fluid dynamics simulation based on the estimated outlet flow rate of the stenosis and the estimated resistance of the stenosis.

13. The method of claim 12, further comprising:
determining a fractional flow reserve for the steno sis based on a result of the subsequent computational fluid dynamics simulation.

14. A system, comprising:
a data analyzer with a processor configured to determine a fractional flow reserve classification of an unknown fractional flow reserve for a stenosis, the processor, including:
- a boundary condition estimator configured to estimate at least one boundary condition of a stenosis of a vessel, including at least one of an estimated outlet flow rate of the stenosis or an estimated outlet resistance of the stenosis, based on image data that includes a representation of the vessel and the stenosis, wherein the image data is generated by one of a one a computed tomography, an X-ray, or a magnetic resonance imaging modality,
wherein the boundary condition estimator estimates an outlet flow rate of the stenosis as a function of an effective diameter or radius at an outlet of the stenosis, a diameter or radius at an inlet of the stenosis, and a flow rate at the inlet of the stenosis, and the boundary condition estimator estimates a resistance of the stenosis based an aortic blood pressure at the inlet of the stenosis and the outlet flow rate using an iterative algorithm;
- a feature extractor configured to extract one or more features from at least one of segmented tissue of interest in image data representing the stenosis and corresponding vessel, the estimated boundary conditions of the stenosis, and intensity information from the image data or subject data;
- a classifier configured to classify the unknown fractional flow reserve into one of a plurality of different pre-defined classes based on the extracted features, including the estimated outlet flow rate of the stenosis and the estimated outlet resistance of the stenosis extracted features, and a learning model; and
- a FFR estimator configured to estimate a point estimation of the fractional flow reserve for the stenosis using a weighted interpolation based on at least one of a predetermined number of nearest neighbor samples of a training set or only from a related class set from the training set, where the related class set is a class corresponding to the classification class.

15. The system of claim 14, the data analyzer, further comprising:
a confidence interval determiner configured to determine a confidence interval of the estimated fractional flow reserve.

16. The system of claim 14, further comprising:
a parameter determiner configured to determine the flow rate at the inlet of the stenosis using a machine learning algorithm trained with patient data, including at least one of image or non-image data, and flow rates measurements of other patients determined via cardiac catheterization.

17. The system of claim 14, wherein the boundary condition estimator estimates a velocity for the stenosis based on the flow rate.

18. The system of claim 14, the data analyzer, further comprising:
- a CFD processor configured to perform a computational fluid dynamics simulation based on the at least one boundary condition; and
- a FFR determiner configured to determine an FFR for the stenosis based on a result of the CFD processor.

19. A method, comprising:
estimating an outlet flow rate of a stenosis based on an effective diameter or radius at an outlet of the stenosis, a diameter or radius at an inlet of the stenosis, and a flow rate at the inlet of the stenosis, where at least one of the effective diameter or radius, the diameter or radius or the flow rate is determined based on image data produced by one of a computed tomography, an X-ray, or a magnetic resonance imaging system;

estimating a resistance of the stenosis based on aortic blood pressure at the inlet of the stenosis, the outlet flow rate, and a course computational fluid dynamics simulation;

classifying an unknown fractional flow reserve metric for a cardiac vessel with the stenosis as one of a plurality of different pre-defined classes based on extracted features and a learning model, wherein the extracted features include one or more estimated boundary conditions of the stenosis, including at least one of the estimated outlet flow rate or the estimated outlet resistance of the stenosis;

generating a signal indicative of the classification;

estimating a point estimation of a fractional flow reserve for the stenosis and generating a second signal indicative thereof; and using a weighted interpolation based on at least one of a predetermined number of nearest neighbor samples of a training set or only from a related class set from the training set, where the related class set is a class corresponding to the classification class.

* * * * *